(12) United States Patent
Wang et al.

(10) Patent No.: US 10,995,087 B2
(45) Date of Patent: May 4, 2021

(54) CRYSTAL FORM OF URAT1 INHIBITOR, AND PREPARATION METHOD THEREFOR

(71) Applicant: MEDSHINE DISCOVERY INC., Jiangsu (CN)

(72) Inventors: Jianfei Wang, Shanghai (CN); Yang Zhang, Shanghai (CN); Wenyuan Zhu, Shanghai (CN); Jian Li, Shanghai (CN); Shuhui Chen, Shanghai (CN)

(73) Assignee: MEDSHINE DISCOVERY INC., Nanjing (CN)

( * ) Notice: Subject to any disclaimer, the term of this patent is extended or adjusted under 35 U.S.C. 154(b) by 0 days.

(21) Appl. No.: 16/765,922

(22) PCT Filed: Nov. 20, 2018

(86) PCT No.: PCT/CN2018/116351
§ 371 (c)(1),
(2) Date: May 21, 2020

(87) PCT Pub. No.: WO2019/101058
PCT Pub. Date: May 31, 2019

(65) Prior Publication Data
US 2020/0361917 A1    Nov. 19, 2020

(30) Foreign Application Priority Data
Nov. 23, 2017    (CN) .......................... 201711181960.2

(51) Int. Cl.
*C07D 409/04*    (2006.01)
(52) U.S. Cl.
CPC ........ *C07D 409/04* (2013.01); *C07B 2200/13* (2013.01)
(58) Field of Classification Search
CPC ........................... C07D 409/04; C07B 2200/13
See application file for complete search history.

(56) References Cited

U.S. PATENT DOCUMENTS

2016/0108035 A1    4/2016 Peng et al.
2020/0140423 A1    5/2020 Wang et al.

FOREIGN PATENT DOCUMENTS

| CN | 106032377 A | 10/2016 |
| CN | 107266377 A | 10/2017 |
| WO | 2009070740 A2 | 6/2009 |
| WO | 2014183555 A1 | 11/2014 |
| WO | 2017202291 A1 | 11/2017 |

OTHER PUBLICATIONS

International Search Report issued in International Patent Application No. PCT/CN2018/116351 dated Feb. 14, 2019.
Written Opinion issued in International Patent Application No. PCT/CN2018/116351 dated Feb. 14, 2019.
Jul. 21, 2020, Notification of Australian the First Office Action, Application No. 2018370811.
Jul. 6, 2020, Notification of Canadian the First Office Action, Application No. 3,083,295.
Oct. 27, 2020 Japanese Office Action issued in Japanese Patent Application No. 2020528274.
Oct. 21, 2020 Korean Office Action issued in Korean Patent Application No. 1020207018146.
Nov. 26, 2020 European Extended Search Report issued in European Patent Application No. 18880182.3.
Ying Pan et al., Urate Transporter URAT1 Inhibitors: a Patent Review (2012-2015), Expert Opinion on Therapeutic Patents, Jul. 30, 2016, pp. 1129-1138, vol. 26, No. 10.

*Primary Examiner* — Laura L Stockton (57) ABSTRACT

Disclosed are a crystal form of a URAT1 inhibitor, and a preparation method therefor.

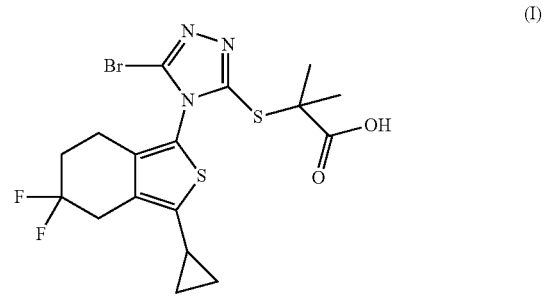

(I)

14 Claims, 6 Drawing Sheets

CRYSTAL FORM OF URAT1 INHIBITOR, AND PREPARATION METHOD THEREFOR

CROSS-REFERENCE TO RELATED APPLICATIONS

CN201711181960.2, filed on 2017 Nov. 23.

TECHNICAL FIELD

The invention relates to a crystal form of a URAT1 inhibitor and a preparation method therefor.

BACKGROUND ART

Uric acid is a metabolic product of purine compounds in animals. For humans, due to the lack of uricase capable of continuing to oxidize and degrade uric acid in the body, uric acid is excreted through the intestine and the kidney as the final metabolic product of purine in the human body, wherein renal excretion is the main pathway of uric acid excretion in the human body. The upper limit of the normal uric acid concentration range in the human body is 400 μmol/L (6.8 mg/dL) for males and 360 μmol/L (6 mg/dL) for females. Abnormal uric acid levels in the human body are often due to increased uric acid production or decreased uric acid excretion. Diseases associated with abnormal uric acid levels include hyperuricemia, gout, etc.

Hyperuricemia is a disorder of metabolism of purine substances in the human body, which results in an increase of the synthesis of uric acid or decrease of excretion of uric acid in the human body and an abnormally high level of uric acid in the blood. Gouty arthritis refers to when the concentration of uric acid in the human blood exceeds 7 mg/dL, uric acid is deposited in the form of monosodium salt in joints, cartilage and kidneys, resulting in painful inflammation due to the overreaction (sensitivity) of the body's immune system. The general attack site is the big toe joint, ankle joint, knee joint, etc. Red, swollen, hot and severe pain appear in the attack site of acute gout, which usually occurs at midnight to wake people from sleep. In the early stage of gout, onset is more common in the joints of the lower limbs. Hyperuricemia is the pathological basis of gout arthritis, and the use of drugs to reduce the concentration of uric acid in the blood is one of the common methods for preventing gouty arthritis.

In Europe and the United States, the onset of hyperuricemia and gout disease is on the rise. Epidemiological studies have shown that the incidence of gouty arthritis accounts for 1-2% of the total population as the most predominant type of arthritis in adult men. Bloomberg estimates that there will be 17.7 million patients with gout in 2021. In China, the survey shows that 25.3% of the population aged 20-74 has high levels of blood uric acid and 0.36% suffers from gout disease. At present, clinical treatment drugs mainly include 1) drugs that inhibit uric acid production, such as xanthine oxidase inhibitors allopurinol and febuxostat; 2) drugs that promote uric acid excretion, such as probenecid and benzbromarone; 3) inflammation inhibitors, such as colchicine, etc. These drugs have certain defects in treatment, such as poor efficacy, large side effects and high cost, which are the main bottlenecks of their clinical application. It has been reported that 40%-70% of patients do not reach the expected treatment target (<6 mg/dL) after receiving standard procedure treatment.

As a uric acid excretion promoter, its mechanism is to reduce the reabsorption of uric acid by inhibiting the URAT1 transporter on the brush border membrane of proximal convoluted renal tubules. Uric acid is a metabolic product of purines in the body, which is mainly filtered by the glomeruli in the original form, reabsorbed and re-secreted by renal tubules, and finally excreted from the body through urine and very few of which can be secreted into the intestinal cavity by mesenteric cells. The S1 segment of the proximal convoluted renal tubule is the place of uric acid reabsorption, and 98% to 100% of the filtered uric acid enters the epithelial cells through the uric acid transporter URAT1 and the organic anion transporter OAT4 on the brush border membrane of the tubular epithelial cells. The uric acid that enters the epithelial cells is reabsorbed into the capillaries around the tubules via the renal tubule basal lateral membrane. The S2 segment of the proximal convoluted renal tubule is the place of uric acid re-secretion, and the amount of secretion is about 50% of the amount of glomerular filtration. The uric acid in the renal interstitium first enters the epithelial cells via the anion transporters OAT1 and OAT3 on the basal lateral membrane of renal tubular epithelial cells. The uric acid that enters the epithelial cells is then discharged into the renal tubules via another anion transporter, MRP4, on the brush border membrane. The S3 segment of the proximal convoluted renal tubule may be the place of reabsorption after uric acid secretion. The amount of the reabsorption is about 40% of the amount of glomerular filtration, and similar to the first step of reabsorption, URAT1 may be a key reabsorption transporter. Therefore, if the urate transporter URAT1 can be significantly inhibited, the excretion of uric acid in the body will be enhanced, thereby reducing the level of blood uric acid and thus the possibility of gout attacks.

In December 2015, the FDA of U.S. approved the use of the first URAT1 inhibitor Zurampic (Leinurad) at 200 mg dose in combination with xanthine oxidase inhibitor XOI (such as Febuxostat, etc.) for the treatment of hyperuricemia and gouty arthritis. However, compared with the use of the xanthine oxidase inhibitors alone, the additive effect of the use in combination is not very significant. The 400 mg dose of Zurampic was not approved due to the significant toxic side effects (incidence of kidney-related adverse events, especially kidney stone) at high doses. Therefore, the FDA requires a black-box warning labelling for Zurampic to warn medical personnel of the risk of acute renal failure caused by Zurampic, which is more common when it is not used in combination with XOI, and if Zurampic is used in an over-approved dose, the risk of renal failure is higher. Meanwhile, the FDA required that after Zurampic was marketed, AstraZeneca should continue to investigate the safety of Zurampic on the kidney and cardiovessel. Therefore, the development of a novel and safe blood uric acid-lowering medicine has become a strong demand in this field.

WO2009070740 discloses Leinurad, which has the structure as follows:

Content of the Invention

The present invention provides a crystal form A of a compound of formula (I) having characteristic diffraction peaks at 2θ angles of 7.50±0.2°, 13.04±0.2°, and 21.43±0.2° in the X-ray powder diffraction pattern thereof.

In some embodiments of the present invention, the crystal form A has characteristic diffraction peaks at 2θ angles of 7.50±0.2°, 9.66±0.2°, 13.04±0.2°, 14.42±0.2°, 17.46±0.2°, 18.57±0.2°, 21.43±0.2°, and 26.18±0.2° in the X-ray powder diffraction pattern thereof.

Figure 1:
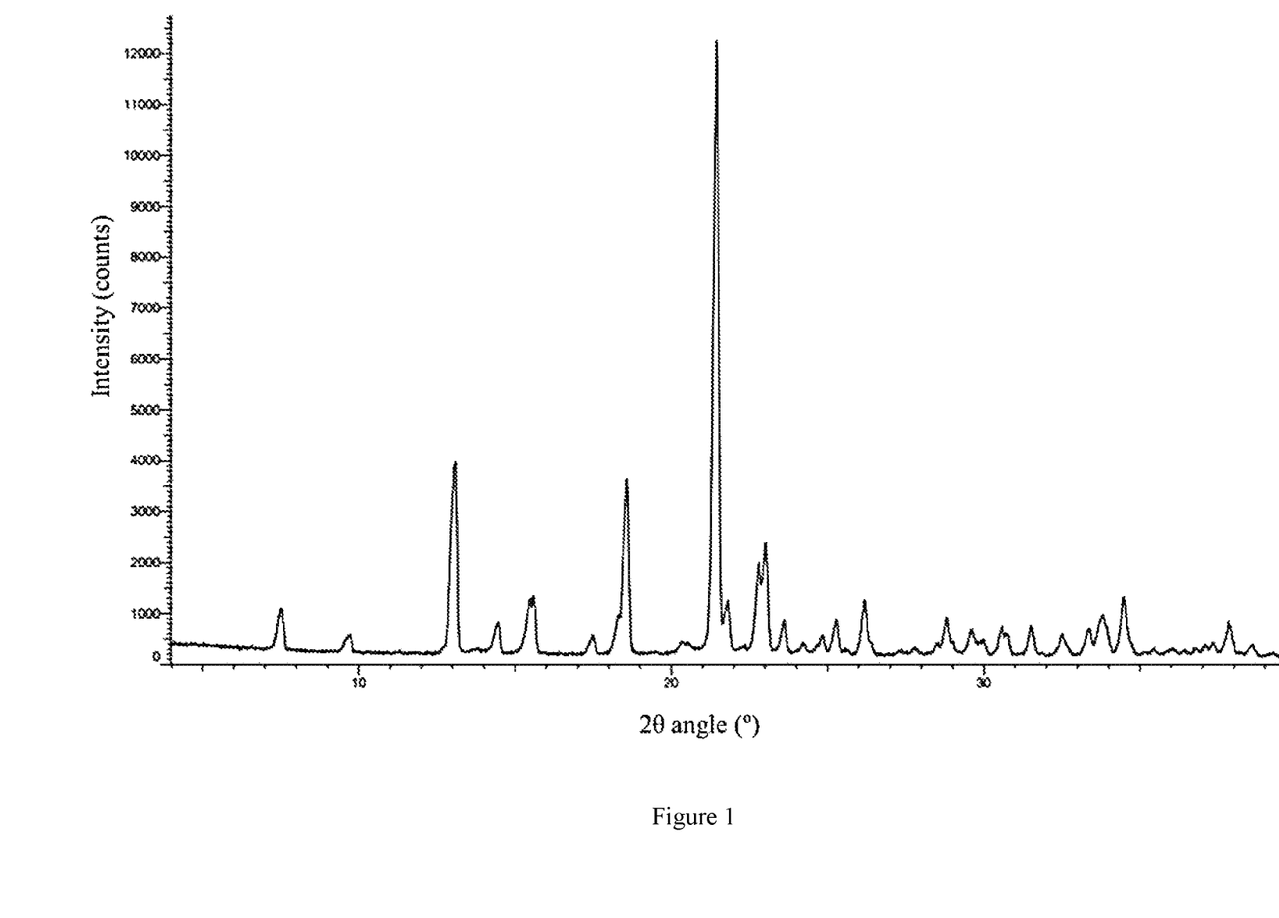
FIG. 1 is the XRPD pattern of Cu-Kα radiation of the crystal form A.

In some embodiments of the present invention, the crystal form A has an XRPD pattern as shown in FIG. 1.

In some embodiments of the present invention, the XRPD pattern analysis data of the crystal form A is as shown in Table 1:

TABLE 1

XRPD pattern analysis data of crystal form A

| No. | 2θ-Angle (°) | d-Spacing (Å) | Relative intensity (%) |
|---|---|---|---|
| 1 | 7.495 | 11.786 | 7.0 |
| 2 | 9.660 | 9.148 | 2.8 |
| 3 | 12.208 | 7.244 | 0.3 |
| 4 | 13.590 | 6.510 | 0.5 |
| 5 | 13.044 | 6.782 | 32.4 |
| 6 | 13.751 | 6.435 | 0.4 |
| 7 | 13.768 | 6.427 | 0.5 |
| 8 | 14.422 | 6.136 | 4.5 |
| 9 | 15.524 | 5.704 | 7.9 |
| 10 | 17.465 | 5.074 | 2.8 |
| 11 | 18.573 | 4.773 | 30.2 |
| 12 | 18.551 | 4.779 | 28.6 |
| 13 | 20.156 | 4.402 | 0.5 |
| 14 | 20.268 | 4.378 | 1.0 |
| 15 | 20.417 | 4.346 | 1.6 |
| 16 | 20.513 | 4.326 | 1.6 |
| 17 | 21.432 | 4.143 | 100.0 |
| 18 | 21.765 | 4.080 | 7.4 |
| 19 | 22.285 | 3.986 | 0.7 |
| 20 | 22.830 | 3.892 | 13.9 |
| 21 | 22.978 | 3.867 | 16.6 |
| 22 | 23.589 | 3.769 | 5.2 |
| 23 | 24.217 | 3.672 | 1.6 |
| 24 | 24.820 | 3.584 | 2.7 |
| 25 | 25.261 | 3.523 | 5.4 |
| 26 | 25.583 | 3.479 | 0.4 |
| 27 | 26.183 | 3.401 | 9.2 |
| 28 | 27.320 | 3.262 | 0.5 |
| 29 | 27.795 | 3.207 | 1.1 |
| 30 | 28.531 | 3.126 | 1.8 |
| 31 | 28.809 | 3.096 | 6.1 |
| 32 | 29.611 | 3.014 | 4.2 |
| 33 | 29.910 | 2.985 | 2.3 |
| 34 | 30.611 | 2.918 | 4.0 |
| 35 | 30.703 | 2.910 | 3.5 |
| 36 | 31.362 | 2.850 | 1.0 |
| 37 | 31.517 | 2.836 | 5.1 |
| 38 | 32.527 | 2.751 | 3.5 |
| 39 | 33.358 | 2.684 | 4.3 |
| 40 | 33.795 | 2.650 | 6.3 |
| 41 | 34.482 | 2.599 | 9.7 |
| 42 | 35.189 | 2.548 | 0.3 |
| 43 | 35.441 | 2.531 | 0.7 |
| 44 | 36.131 | 2.484 | 0.6 |
| 45 | 36.042 | 2.490 | 0.8 |
| 46 | 36.418 | 2.465 | 0.4 |
| 47 | 36.787 | 2.441 | 0.7 |
| 48 | 37.100 | 2.421 | 1.3 |
| 49 | 37.326 | 2.407 | 1.8 |
| 50 | 37.851 | 2.375 | 5.2 |
| 51 | 38.190 | 2.355 | 0.4 |
| 52 | 38.572 | 2.332 | 1.8 |
| 53 | 39.239 | 2.294 | 0.5 |

In some embodiments of the present invention, the crystal form A has an endothermic peak with an onset point of 169.42±3° C. in the differential scanning calorimetry curve thereof.

Figure 2:
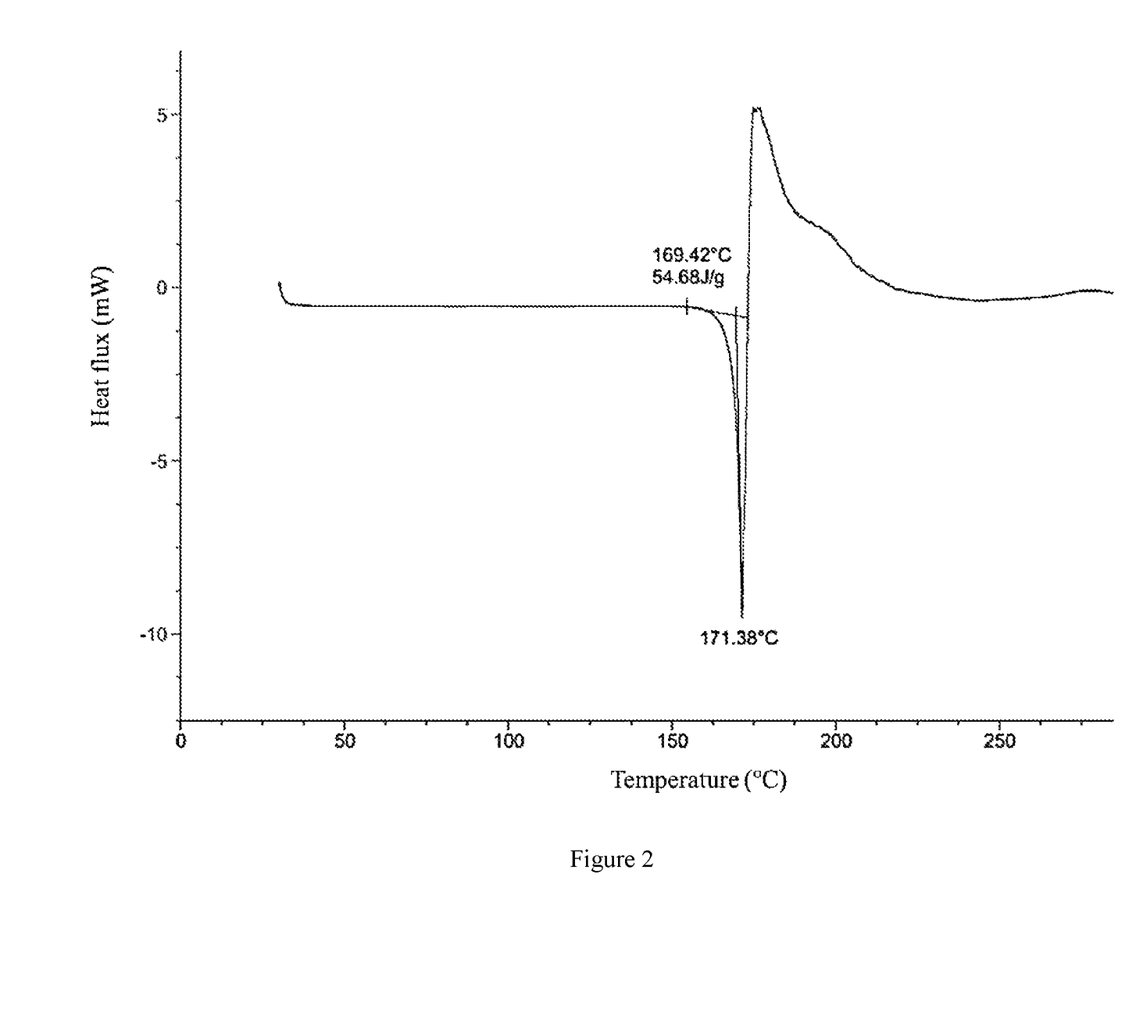
FIG. 2 is the DSC pattern of the crystal form A.

In some embodiments of the present invention, the crystal form A has a DSC pattern as shown in FIG. 2.

In some embodiments of the present invention, the crystal form A has a weight loss of 0.04491% at 100±3° C. in the thermogravimetric analysis curve thereof.

Figure 3:
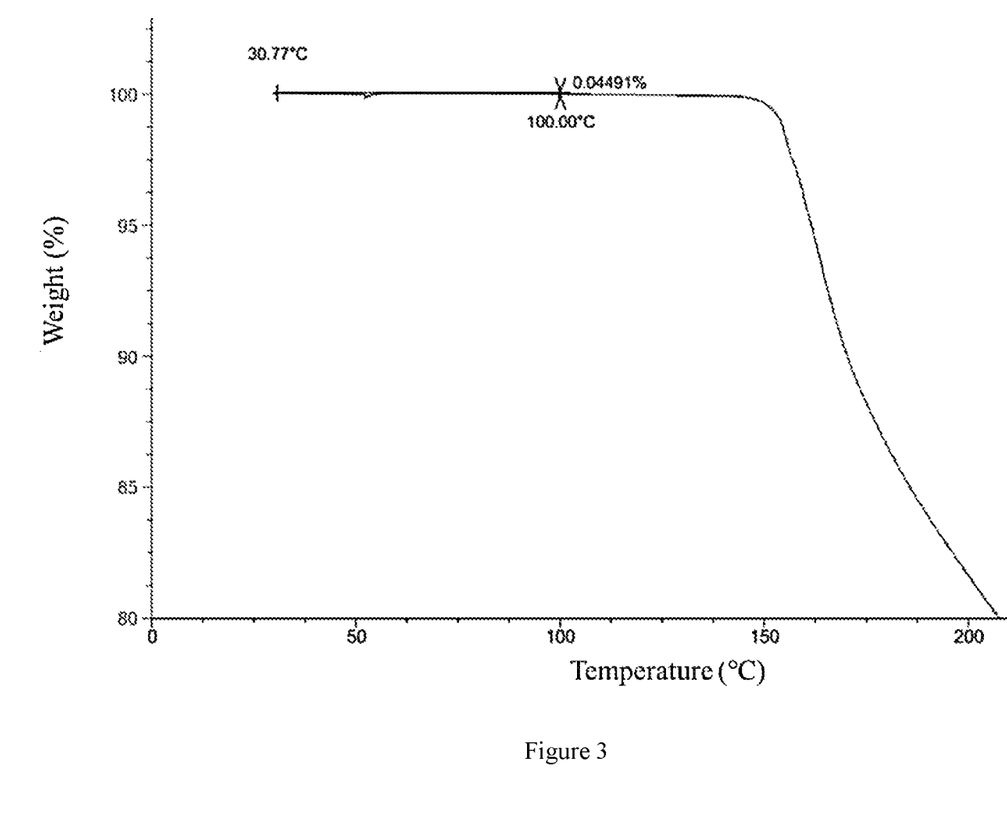
FIG. 3 is the TGA pattern of the crystal form A.

In some embodiments of the present invention, the crystal form A has a TGA pattern as shown in FIG. 3.

The present invention also provides a crystal form B of the compound of formula (I) having characteristic diffraction peaks at 2θ angles of 9.88±0.2°, 10.56±0.2°, and 20.38±0.2° in the X-ray powder diffraction pattern thereof.

In some embodiments of the present invention, the crystal form B has characteristic diffraction peaks at 2θ angles of 9.88±0.2°, 10.56±0.2°, 12.23±0.2°, 13.04±0.2°, 14.62±0.2°, 17.57±0.2°, 20.38±0.2°, and 26.89±0.2° in the X-ray powder diffraction pattern thereof.

Figure 4:
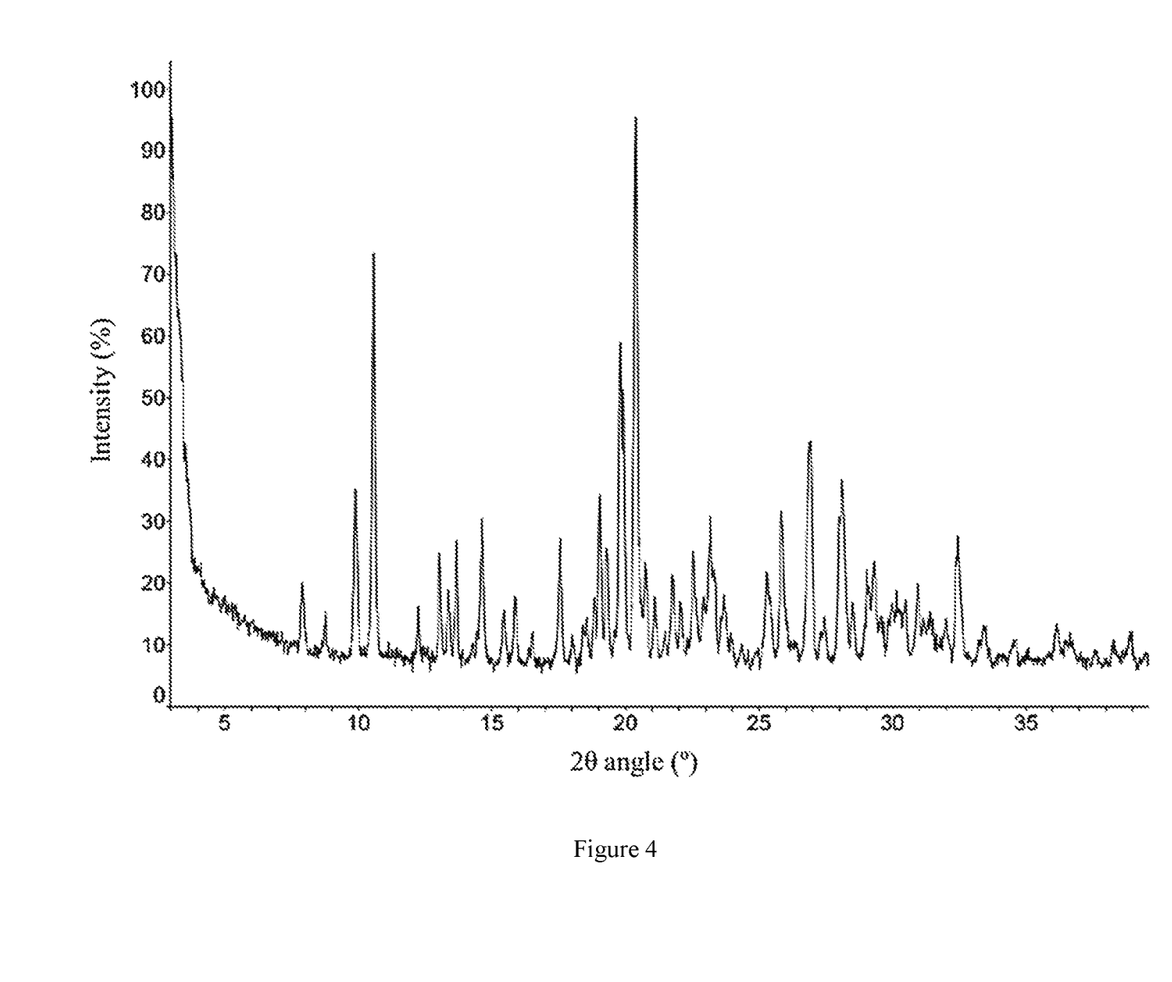
FIG. 4 is the XRPD pattern of Cu-Kα radiation of the crystal form B.

In some embodiments of the present invention, the crystal form B has an XRPD pattern as shown in FIG. 4.

In some embodiments of the present invention, the XRPD pattern analysis data of the crystal form B is as shown in Table 2:

TABLE 2

XRPD pattern analysis data of crystal form B

| No. | 2θ-Angle (°) | d-Spacing (Å) | Relative intensity (%) |
|---|---|---|---|
| 1 | 3.315 | 26.6304 | 52.6 |
| 2 | 3.62 | 24.3886 | 25.2 |
| 3 | 9.885 | 8.9405 | 31.4 |
| 4 | 10.559 | 8.3711 | 75.6 |
| 5 | 12.233 | 7.2291 | 9.9 |
| 6 | 13.04 | 6.7839 | 19.7 |
| 7 | 13.376 | 6.6139 | 12.9 |
| 8 | 13.686 | 6.4646 | 22 |
| 9 | 14.27 | 6.2017 | 3 |
| 10 | 14.62 | 6.0538 | 26.8 |
| 11 | 15.46 | 5.7269 | 8.6 |
| 12 | 15.861 | 5.583 | 12.9 |

TABLE 2-continued

XRPD pattern analysis data of crystal form B

| No. | 2θ-Angle (°) | d-Spacing (Å) | Relative intensity (%) |
|---|---|---|---|
| 13 | 16.52 | 5.3616 | 5.6 |
| 14 | 17.573 | 5.0427 | 23.4 |
| 15 | 18.017 | 4.9195 | 4.9 |
| 16 | 18.546 | 4.7801 | 6.2 |
| 17 | 19.036 | 4.6582 | 29.8 |
| 18 | 19.31 | 4.5929 | 19.2 |
| 19 | 19.803 | 4.4794 | 56.7 |
| 20 | 20.379 | 4.3541 | 100 |
| 21 | 20.737 | 4.2798 | 16.2 |
| 22 | 21.09 | 4.209 | 10.5 |
| 23 | 21.745 | 4.0837 | 14.1 |
| 24 | 22.043 | 4.0291 | 9.3 |
| 25 | 22.548 | 3.94 | 17.6 |
| 26 | 23.179 | 3.8342 | 26.2 |
| 27 | 23.675 | 3.7549 | 9.9 |
| 28 | 24.344 | 3.6533 | 3.4 |
| 29 | 25.292 | 3.5184 | 15.8 |
| 30 | 25.843 | 3.4447 | 27.1 |
| 31 | 26.889 | 3.313 | 40.2 |
| 32 | 27.456 | 3.2458 | 7.7 |
| 33 | 28.11 | 3.1717 | 33.4 |
| 34 | 28.522 | 3.1269 | 10.3 |
| 35 | 29.04 | 3.0723 | 15.9 |
| 36 | 29.294 | 3.0462 | 16.9 |
| 37 | 29.554 | 3.02 | 6.1 |
| 38 | 29.966 | 2.9794 | 8.7 |
| 39 | 30.163 | 2.9604 | 11.2 |
| 40 | 30.495 | 2.9289 | 9.7 |
| 41 | 30.935 | 2.8883 | 12.6 |
| 42 | 31.426 | 2.8443 | 7.7 |
| 43 | 31.982 | 2.7961 | 5.5 |
| 44 | 32.45 | 2.7568 | 22.1 |
| 45 | 33.418 | 2.6792 | 7.1 |
| 46 | 34.583 | 2.5915 | 4.3 |
| 47 | 36.14 | 2.4833 | 6.9 |
| 48 | 36.667 | 2.4488 | 5 |
| 49 | 37.562 | 2.3925 | 2.6 |
| 50 | 38.311 | 2.3474 | 4.3 |
| 51 | 38.899 | 2.3133 | 6.1 |

In some embodiments of the present invention, the crystal form B has an endothermic peak with an onset point of 163.51±3° C. in the differential scanning calorimetry curve thereof.

Figure 5:
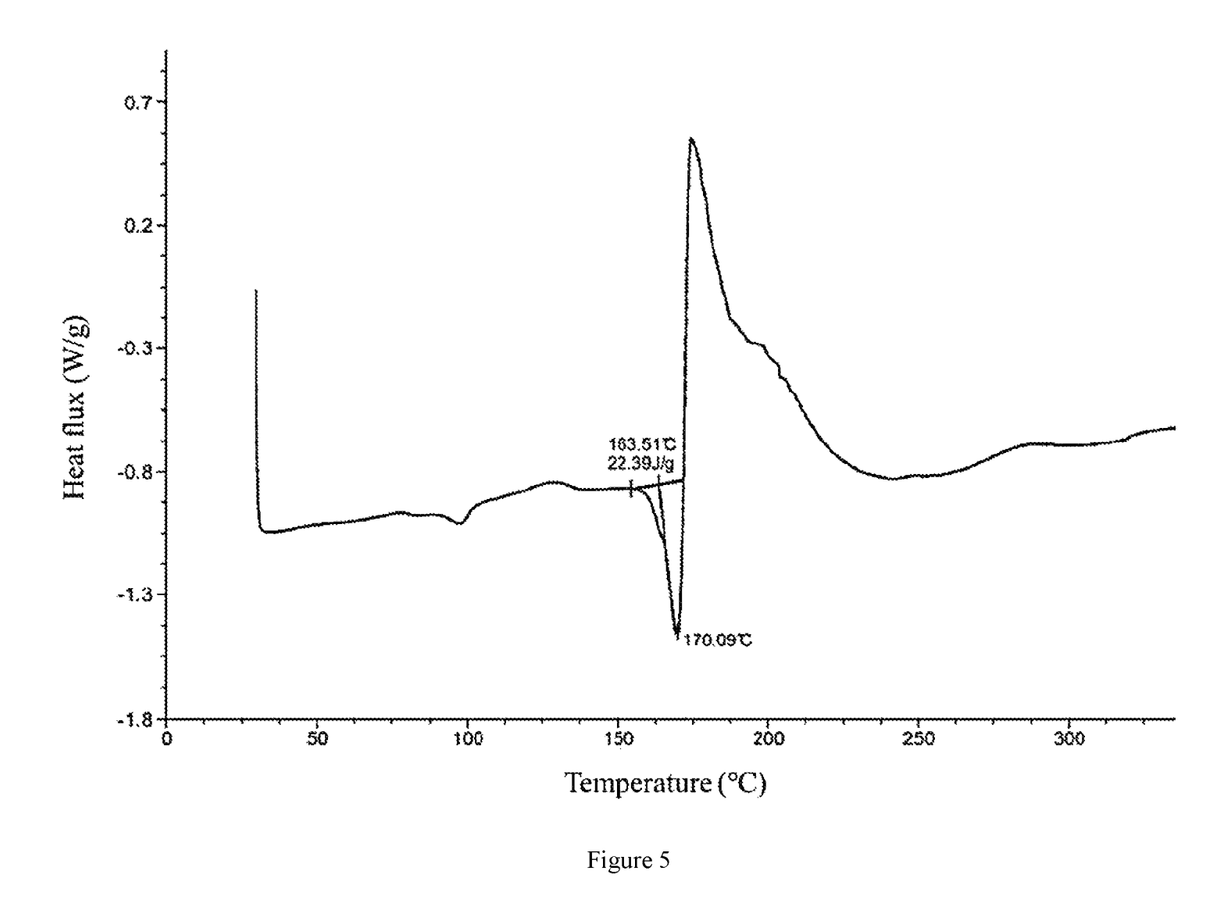
FIG. 5 is the DSC pattern of the crystal form B.

In some embodiments of the present invention, the crystal form B has a DSC pattern as shown in FIG. 5.

In some embodiments of the present invention, the crystal form B has a weight loss of 0.1191% at 120±3° C., and a weight loss of 0.6282% from 120±3° C. to 153.60±3° C. in the thermogravimetric analysis curve thereof.

Figure 6:
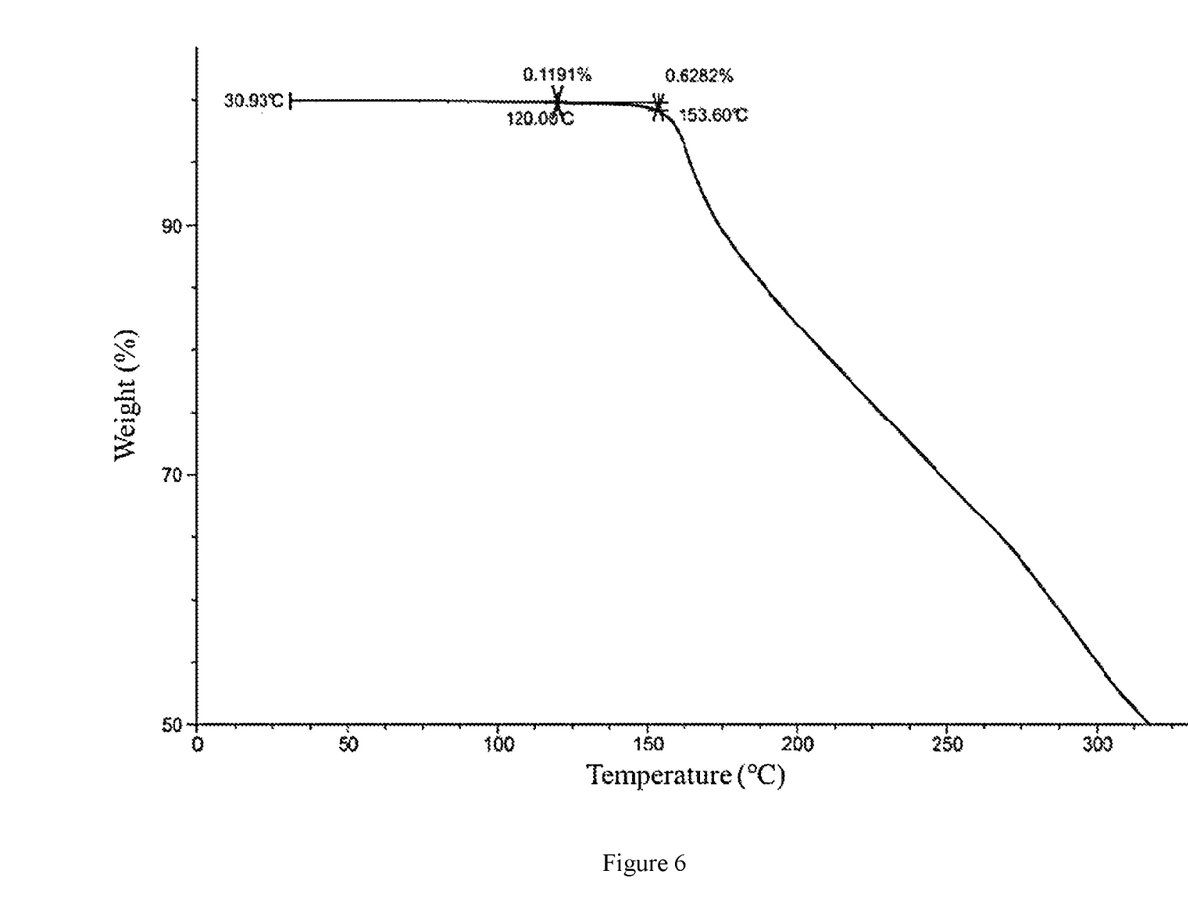
FIG. 6 is the TGA pattern of the crystal form B.

In some embodiments of the present invention, the crystal form B has a TGA pattern as shown in FIG. 6.

Technical Effects

The compound of formula (I) of the present invention exhibits superior in vitro inhibitory activity against URAT1-mediated $^{14}$C-uric acid transport on HEK293 cell lines stably transfected with URAT1 (uric acid transporter) gene. The compound of formula (I) of the present invention has good stability of drug metabolism, and also greatly improves the oral absorption bioavailability of the drug in the meantime; the crystal forms thereof have better solubility and stability. Therefore, the compounds of the present invention have good prospects for medicine.

Definition and Description

Unless otherwise stated, the following terms and phrases used herein are intended to have the following meanings. A particular phrase or term without specific definition should not be considered to be uncertain or unclear, but should be understood in line with its ordinary meaning. When a trade name is used herein, it is intended to refer to its corresponding commercially available product or its active ingredient.

The intermediate compounds of the present invention can be prepared by various synthetic methods well known to those skilled in the art, including the specific embodiments listed below, the embodiments formed by their combination with other chemical synthesis methods, as well as equivalent alternatives well known to those skilled in the art, and preferred embodiments include but are not limited to the examples of the present invention.

The chemical reaction of the specific embodiment of the present invention is carried out in an appropriate solvent, which should be suitable for the chemical changes of the present invention and the reagents and materials required. In order to obtain the compound of the present invention, those skilled in the art sometimes need to modify or select the synthesis steps or reaction processes based on the existing embodiments.

Hereinafter, the present invention will be described in details by reference to the examples which do not indicate any limitation to the present invention.

All solvents used in the present invention are commercially available and can be used without further purification.

The solvent used in the present invention is commercially available. The following abbreviations are used in the present invention: DCM stands for dichloromethane; DMF stands for N,N-dimethylformamide; DMSO stands for dimethyl sulfoxide; EtOH stands for ethanol; MeOH stands for methanol; TFA stands for trifluoroacetic acid; TsOH stands for p-toluene sulfonic acid; mp stands for melting point; EtSO3H stands for ethanesulfonic acid; MeSO$_3$H stands for methanesulfonic acid; ATP stands for adenosine triphosphate; HEPES stands for 4-hydroxyethylpiperazine ethanesulfonic acid; EGTA stands for ethylene glycol bis(2-aminoethyl ether) tetraacetic acid; MgCl$_2$ stands for magnesium dichloride; MnCl$_2$ stands for manganese dichloride; DTT stands for dithiothreitol.

X-Ray Powder Diffractometer (XRPD)

Instrument model: Bruker D8 Advance X-ray Diffractometer

Test method: approximately 10-20 mg sample was used for XRPD detection.

The detailed XRPD parameters were as follows:
X-ray tube: Cu, ka, (k=1.54056 Å).
X-ray tube voltage: 40 kV, X-ray tube current: 40 mA
Divergence slit: 0.60 mm
Detector slit: 10.50 mm
Anti-scatter slit: 7.10 mm
Scan range: 4-40 deg (or 3-40 deg)
Step diameter: 0.02 deg
Step length: 0.12 second
Rotation speed of sample tray: 15 rpm

Differential Scanning Calorimeter (DSC)

Instrument model: TA Q2000 Differential Scanning calorimeter

Test method: A sample (~1 mg) was placed in a DSC aluminum pan for testing, and the sample was heated from 25° C. to 300° C. at a heating rate of 10° C./min under N$_2$ at a flow rate of 50 mL/min.

Thermal Gravimetric Analyzer (TGA)

Instrument model: TA Q5000IR thermal gravimetric analyzer

Test method: A sample (2-5 mg) was placed in a TGA platinum pot for testing, and the sample was heated from room temperature to a weight loss of 20% at a heating rate of 10° C./min under $N_2$ at a flow rate of 25 mL/min.

DETAILED DESCRIPTION OF THE EMBODIMENTS

In order to understand the content of the present invention better, the following detailed description will be made in combination with specific examples, but the specific embodiments are not a limitation to the content of the present invention.

Example 1: Preparation of the Compound of Formula (I)

(I)

Synthetic Route:

1

Step 1: Synthesis of Compound 2

4.5 L of dimethyl sulfoxide was added to a three-necked flask (10 L), and potassium tert-butoxide (836.66 g, 7.46 mol, 2 eq) was added under stirring. The mixture was stirred for 10 minutes after the completion of the addition until the mixture was dissolved to be clarified. And then the internal temperature of the reaction solution was cooled to 20-25° C. using an ice water bath. A solution of compound 1 (500.05 g, 3.73 mol, 1 eq) in dimethyl sulfoxide (500 mL) was added dropwise to the above solution, and stirred for 30 minutes after the addition. Then, carbon disulfide (283.86 g, 3.73 mol, 1 eq) was added dropwise, and after the completion of the addition, the reaction was continued for 30 minutes under stirring. Then, ethyl bromoacetate (1250 g, 7.46 mol, 2 eq) was added dropwise, and the mixture was reacted for 2 hours under stirring after the addition. Finally, potassium carbonate (515.52 g, 7.46 mol, 1 eq) was added, and the internal temperature was raised to 65° C., and the reaction was continued for 8 hours under stirring. After the completion of the reaction, the reaction solution was cooled to room temperature. The reaction solution was diluted with ethyl acetate (10 L), then 1M hydrochloric acid (2 L) and water (2 L) were added and the mixture was stirred for 10 minutes and was allowed to stand and separate. The aqueous phase was separated, and the organic phase was washed with water (2 L×3). The aqueous phases were combined and extracted with ethyl acetate (3 L). All organic phases were combined and washed with saturated brine (2 L×2). The organic phase was dried with an appropriate amount of anhydrous sodium sulfate, the desiccant was removed by filtration, and the solvent was removed from the filtrate under reduced pressure to obtain a crude product. In the same scale, 6 batches were fed in parallel, and a black-red oily crude product was obtained after the combination. After the crude product was allowed to stand for 72 hours, a large amount of solid was precipitated. Ethanol (2 L) was added thereto, the mixture was stirred for 30 minutes, filtered, the filter cake was collected and dried under vacuum to obtain compound 2. $^1$H NMR (400 MHz, CDCl$_3$) δ: 4.32 (q, J=7.2 Hz, 2H), 4.19 (q, J=7.2 Hz, 2H), 3.56 (s, 2H), 3.25 (t, J=6.8 Hz, 2H), 3.19 (t, J=14.4 Hz, 2H), 2.26-2.17 (m, 2H), 1.37 (t, J=7.2 Hz, 3H), 1.27 (t, J=7.2 Hz, 3H); MS m/z=364.8 [M+H]$^+$.

Step 2: Synthesis of Compound 3

Compound 2 (241.00 g, 0.66 mol) was dissolved in ethanol (1 L) and placed in an autoclave (5 L). Raney nickel (120 g) was added under the protection of argon, followed by the addition of ethanol (2 L). The autoclave was installed and replaced with argon for three times and then with hydrogen for three times, and filled with hydrogen to a pressure of 2.0 MP in the autoclave, the mixture was stirred and heated to 85° C. in the autoclave and reacted for 28 hours. The reaction was stopped, and the reaction system was cooled to room temperature, the reaction solution was filtered, and the filter cake was rinsed with ethanol for three times, 0.5 L each time. The filtrates were combined and then dried by rotary evaporation to obtain compound 3. $^1$H NMR (400 MHz, CDCl$_3$) δ: 7.09 (s, 1H), 4.26 (q, J=7.2 Hz, 2H), 3.20 (t, J=6.8 Hz, 2H), 3.12 (t, J=14.4 Hz, 2H), 2.20-2.10 (m, 2H), 1.30 (t, J=6.8 Hz, 3H); MS m/z=247.0 [M+H]t Step 3: Synthesis of Compound 4

Compound 3 (406.2 g, 1.65 mol, 1 eq) was dissolved in acetonitrile (6 L), then N-bromosuccinimide (1484.2 g, 6.60 mol, 4 eq) was slowly added, and the resulting reaction solution was reacted under stirring for 12 hours at 23-25° C. After the completion of the reaction, the reaction liquid was concentrated to about 1.0 L. The solid was removed by filtration, and a saturated solution of sodium bisulfite (1 L) was added to the filtrate and stirred for 10 minutes. Ethyl acetate was added and extracted for three times, 2 L each time. The organic phases were combined and dried by adding an appropriate amount of anhydrous sodium sulfate. The desiccant was removed by filtration, and the filtrate was concentrated under reduced pressure. Petroleum ether (3 L) was added to the residue, and stirred thoroughly for 30 minutes at 30° C. After filtration, the filter cake was washed five times with petroleum ether, 200 mL each time, until no product remained in the filter cake. All organic phases were combined and dried by rotary evaporation to obtain a crude product. Petroleum ether (100 mL) was added to the crude product, stirred thoroughly, filtered, and the filter cake was collected and dried under vacuum to obtain compound 4. $^1$H NMR (400 MHz, CDCl$_3$) δ: 4.24 (q, J=7.2 Hz, 2H), 3.19 (t, J=6.8 Hz, 2H), 2.95 (t, J=14.4 Hz, 2H), 2.17-2.07 (m, 2H), 1.29 (t, J=7.2 Hz, 3H).

Step 4: Synthesis of Compound 5

Compound 4 (340.21 g, 1.05 mol), cyclopropylboronic acid (108.12 g, 1.26 mol), anhydrous potassium phosphate (444.98 g, 2.10 mol), palladium acetate (12.03 g, 53.58 mmol) and 2-dicyclohexyl phosphorus-2',4',6'-triisopropyl-biphenyl (23.86 g, 50.05 mmol) were added to a mixed solvent of toluene and water (10:1, 3.4 L/340 mL), and after the atmosphere in the reaction flask was replaced with nitrogen for six times, it was placed in an oil bath. The reaction solution was heated at an internal temperature of 80° C., and was reacted under stirring at this temperature for 16 hours. After the completion of the reaction, the reaction solution was cooled to room temperature, and trithiocyanuric acid (6.51 g suspended in 34 mL of ethanol) was added to the reaction solution and stirred for 0.5 hour. In a similar scale (300.00 g of compound 4), 5 batches were fed in parallel and combined for processing. The resultant was filtered, the organic phase was separated, and the aqueous phase was extracted with ethyl acetate (250 mL×2). The organic phases were combined and dried by adding an appropriate amount of anhydrous sodium sulfate. The desiccant was removed by filtration, and the filtrate was concentrated under reduced pressure to obtain a black oily crude product. After the crude product was allowed to stand for 20 hours, a yellow solid was precipitated, and petroleum ether (3 L) was added thereto and stirred for an hour. After filtration, the filter cake was dried under vacuum to obtain compound 5. $^1$H NMR (400 MHz, CDCl$_3$) δ: 4.29 (q, J=7.2 Hz, 2H), 3.23 (t, J=6.4 Hz, 2H), 3.16 (t, J=14.8) Hz, 2H), 2.24-2.18 (m, 2H), 1.95-1.85 (m, 1H), 1.35 (t, J=6.8 Hz, 3H), 1.09-1.07 (m, 2H), 0.77-0.75 (m, 2H).

Step 5: Synthesis of Compound 6

Compound 5 (619.27 g, 2.16 mol) was added to a solution of sodium hydroxide (173.55 g, 4.33 mol) in mixed ethanol and water (3 L/3 L), and the reaction solution was heated to an internal temperature of 60° C. and reacted under stirring for 3 hours. After the completion of the reaction, the reaction solution was cooled to room temperature. In a similar scale (750.17 g of compound 5), one batch was fed in parallel and combined for processing. The combined reaction solution was extracted with petroleum ether (4 L). The organic phase was separated, and the organic phase was backwashed twice with water (1.5 L×2). The aqueous phases were combined and concentrated under reduced pressure to remove ethanol. Water was added to the aqueous phase to dilute to 13 L, then diluted hydrochloric acid (3M) was slowly added to adjust the pH to 2, and a large amount of light yellow solid precipitated. After filtration, the filter cake was rinsed with water (3.0 L×2). The filter cake was collected after being filtered under vacuum, and dried under vacuum at 60° C. in a vacuum oven to obtain compound 6. $^1$H NMR (400 MHz, DMSO-d$_6$) δ: 12.79 (brs, 1H), 3.23 (t, J=14.8 Hz, 2H), 3.07 (t, J=6.8 Hz, 2H), 2.27-2.20 (m, 2H), 2.19-2.02 (m, 1H), 1.09-1.04 (m, 2H), 0.68-0.66 (m, 2H).

Step 6: Synthesis of Compound 7

Compound 6 (641.27 g, 2.48 mol), triethylamine (754.07 g, 7.45 mol) and diphenylphosphoryl azide (1025.34 g, 3.73 mol) were added to tert-butanol (6.5 L) under stirring. The reaction solution was placed in an oil bath at 100° C. and heated for 16 hours. After the completion of the reaction, the reaction solution was cooled to room temperature. In a similar scale (650.00 g of compound 6), 4 batches were fed in parallel and combined for processing. The reaction solution was combined and concentrated under reduced pressure to remove tert-butanol. The remaining black residue was dissolved with ethyl acetate (10 L), and the resulting ethyl acetate solution was washed with aqueous sodium hydroxide solution (5%, 5.0 L×2), and then washed with saturated brine (5.0 L). An appropriate amount of anhydrous sodium sulfate was added for drying. The desiccant was removed by filtration, and the filtrate was concentrated under reduced pressure to obtain a brown-black solid crude product. A solid precipitated after standing. Petroleum ether (8 L) was added to the crude product and stirred for 2 hours. After filtration, the filter cake was rinsed with petroleum ether (1 L) in portions, and the filter cake was dried under vacuum at 60° C. in a vacuum oven to obtain compound 7. $^1$H NMR (400 MHz, CDCl$_3$) δ: 6.31 (brs, 1H), 3.11 (t, J=14.8 Hz, 2H), 2.66 (t, J=6.8 Hz, 2H), 2.23-2.15 (m, 2H), 1.82-1.75 (m, 1H), 1.51 (s, 9H), 0.94-0.90 (m, 2H), 0.68-0.65 (m, 2H).

Step 7: Synthesis of Compound 8

Compound 7 (1199.17 g, 3.64 mol) was added to ethyl acetate (2 L), and after stirring evenly, a solution of hydrogen chloride in ethyl acetate (4 L, 16.00 mol, 4 M) was added. The reaction solution was reacted at 15° C. for 2.5 hours and then placed in a warm water bath at 40° C. to react for another 2 hours. After the completion of the reaction, a large amount of dark red solid precipitated. After filtration, the filter cake was rinsed with ethyl acetate (2.0 L) in portions. The filter cake was dried under vacuum at 60° C. in a vacuum oven to obtain compound 8. $^1$H NMR (400 MHz, DMSO-d$_6$) δ: 3.17 (t, J=14.8 Hz, 2H), 2.82 (t, J=6.8 Hz, 2H), 2.25-2.15 (m, 2H), 2.00-1.94 (m, 1H), 0.99-0.95 (m, 2H), 0.58-0.54 (m, 2H); MS m/z=229.8 [M+H-HCl]$^+$.

Step 8: Synthesis of Compound 9

In a 3 L three-necked flask, compound 8 (301.25 g) was added to tetrahydrofuran (600 mL), and the mixture was cooled under stirring to an internal temperature of 0-10° C. in an ice-water bath. Diisopropylethylamine (635.72 g) was added dropwise, and the ice water bath was removed after the completion of the addition, and the mixture was stirred at an internal temperature of 10-15° C. for about 10 minutes.

After filtration, the filter cake was washed with tetrahydrofuran (100 mL×2). The filtrates were combined to obtain a solution A for use.

Tetrahydrofuran (2 L) was added to a 5 L reaction flask containing thiophosgene (257.48 g). The mixture was cooled under stirring to an internal temperature of 0-10° C. in an ice-water bath, and the solution A was slowly added dropwise, the addition was completed within about 5.5 hours of heat preservation, and stirring was continued for 10 minutes. After the completion of the reaction, the reaction mixture was filtered, and the filter cake was washed with tetrahydrofuran (150 mL×2). The filtrates were combined and concentrated under reduced pressure to remove the solvent. Tetrahydrofuran (400 mL) was added to the residue and dissolved to obtain a solution B for use.

Hydrazine hydrate (112.94 g) was added to tetrahydrofuran (2.5 L), and cooled under stirring in an ice water bath to an internal temperature of 5-10° C. The solution B was added dropwise, the addition was completed within about 2 hours of heat preservation, and stirring was continued for 10 minutes. After the completion of the reaction, the reaction was stopped. The ice water bath was removed, N,N-dimethylformamide dimethyl acetal (333.45 g) was added, and heated to an internal temperature of 60-65° C., and after keeping the temperature and reacting for 3 hours, the reaction was stopped.

The reaction solution was dried by rotary evaporation, ethyl acetate (2 L) and pure water (1 L) were added to the residue, and stirred evenly. The pH was adjusted to 5-6 with 10% hydrobromic acid, and the mixture was continually stirred for 5 minutes, and was allowed to stand for 10 minutes. The solution was separated to obtain the aqueous phase. The organic phase was washed with pure water (500 mL×2). The aqueous phases were combined and extracted with ethyl acetate (1 L), and the organic phases were combined and dried by adding an appropriate amount of anhydrous sodium sulfate. The desiccant was removed by filtration, and the filtrate was concentrated to dryness under reduced pressure to obtain a crude product of compound 9. N-heptane (2.0 L) and tert-butyl methyl ether (150 mL) were added to the crude product, the mixture was slurried (rotation speed of stirring 550 rpm) for 18 hours. After filtration, the filter cake was washed with n-heptane (150 mL). The filter cake was collected, and dried under vacuum at 60° C. in a vacuum oven to obtain compound 9. $^1$H NMR (400 MHz, CDCl$_3$) δ: 7.82 (s, 1H), 3.20 (t, J=14.8 Hz, 2H), 2.74 (t, J=6.8 Hz, 2H), 2.28-2.10 (m, 2H), 1.98-1.82 (m, 1H), 1.06-1.02 (m, 2H), 0.75-0.71 (m, 2H); MS m/z=313.9 [M+H]$^+$.

Step 9: Synthesis of Compound 10

Acetonitrile (3 L) was added to a 5 L three-necked flask. Compound 9 (303.25 g) and potassium carbonate (261.83 g) were added first under stirring. Then, methyl 2-bromoisobutyrate (203.85 g) was added, and after replacing the reaction system with nitrogen, it was heated to an internal temperature of 60-65° C., the temperature was maintained, and the mixture was reacted for 2 hours. After the completion of the reaction, the heating was stopped, and the mixture was naturally cooled to 15-20° C. under stirring. After filtration, and the filter cake was washed with ethyl acetate (100 mL×3). The filtrate was combined and concentrated under reduced pressure to dryness to obtain a crude product. The crude product was purified by column chromatography (mobile phase: ethyl acetate/n-heptane=1:5-2:1) to obtain compound 10. $^1$H NMR (400 MHz, CDCl$_3$) δ: 8.20 (s, 1H), 3.68 (s, 3H), 3.19 (t, J=14.4 Hz, 2H), 2.57 (t, J=6.8 Hz, 2H), 2.22-2.12 (m, 2H), 1.93-1.83 (m, 1H), 1.67 (s, 6H)), 1.08-1.03 (m, 2H), 0.73-0.69 (m, 2H); MS m/z=414.0 [M+H]$^+$.

Step 10: Synthesis of Compound 11

Acetonitrile (3.17 L) was added to a 5 L three-necked flask. Compound 10 (317.22 g) and thiocarbonyl diimidazole (26.94 g) were added under stirring, and the mixture was maintained at 16-20° C. and stirred for 5 minutes. N-bromosuccinimide (158.60 g) was added, the temperature was maintained, and the mixture was stirred for 30 minutes. After the completion of the reaction, the reaction was stopped. After filtration, the filtrate was concentrated under reduced pressure to obtain a black crude product. The crude product was purified by column chromatography (mobile phase: ethyl acetate/n-heptane=0-50%) to obtain 340.62 g of yellow solid crude product. This crude product was dissolved in ethyl acetate (3.50 L), and then washed with pure water (700 mL×4). The organic phase was separated, and the organic phase was dried by adding an appropriate amount of anhydrous sodium sulfate. The desiccant was removed by filtration, and the filtrate was concentrated to dryness under reduced pressure to obtain compound 11. $^1$H NMR (400 MHz, CDCl$_3$) δ: 3.73 (s, 3H), 3.22 (t, J=14.4 Hz, 2H), 2.53 (t, J=6.8 Hz, 2H), 2.24-2.14 (m, 2H), 1.95-1.91 (m, 1H), 1.71 (d, J=4.4 Hz, 6H), 1.11-1.07 (m, 2H), 0.78-0.74 (m, 2H); MS m/z=491.7 [M+H]$^+$, 493.7 [M+H+2]$^+$.

Step 11: Synthesis of Compound of Formula (I)

Tetrahydrofuran (1.2 L) was added to a 5 L reaction flask, and compound 11 (243.03 g) was added under stirring. After dissolution and clarification, pure water (1.2 L) was added, then lithium hydroxide monohydrate (125.46 g) was added, and the mixture was maintained at 20-25° C. and stirred for 2.5 hours. After the completion of the reaction, the reaction was stopped. The reaction solution was concentrated under reduced pressure at 40° C. to remove the organic solvent. Pure water (1 L) was added to the residue, and the organic phase was separated by reverse extraction with tert-butyl methyl ether (300 mL). The water phase was placed in a 10 L three-necked bottle, and the temperature was cooled to 5-10° C. in an ice bath. The pH was adjusted to 2-3 with 40% hydrobromic acid solution, and a large amount of light yellow solid precipitated. The stirring was continued for 30 minutes, and the pH was re-measured to be 2-3 and remained unchanged. The stirring was continued for 20 minutes and filtered. The filter cake was washed with pure water (150 mL×3). The filter cake was collected, and pure water (1500 mL) was added and slurried at room temperature for an hour. After filtration, the filter cake was washed with pure water (150 mL×2), and the filter cake was collected and dried under vacuum at 40° C. for 3 hours to obtain the compound of formula (I). $^1$H NMR (400 MHz, CD$_3$OD) δ: 3.27 (t, J=15.6 Hz, 2H), 2.60-2.47 (m, 2H), 2.27-2.17 (m, 2H), 2.10-2.03 (m, 1H), 1.68 (d, J=1.2 Hz, 6H), 1.15-1.10 (m, 2H), 0.80-0.71 (m, 2H); MS m/z=477.99 [M+H]$^+$, 480.1 [M+H+2]$^+$.

Example 2: Preparation of Crystal Form A of Compound of Formula (I)

The compound of formula (I) (50 mg) was added to a glass bottle, methanol (0.4 mL) was added separately, and stirred into a suspension or solution. The above suspension sample was placed in a constant temperature mixer (40° C.), shaken at 40° C. for 60 hours, and then centrifuged to collect the sample. The aforementioned dissolved and clarified sample was evaporated at room temperature and then centrifuged to collect the sample. The above sample was placed in a vacuum drying oven (40° C.) and dried overnight, and the crystal form was detected by XPRD, the crystal form of the final product was the crystal form A of the compound of formula (I).

The compound of formula (I) (50 mg) was added to a glass bottle, ethyl acetate (0.4 mL) was added separately, and stirred into a suspension or solution. The above suspension sample was placed in a constant temperature mixer (40° C.), shaken at 40° C. for 60 hours, and then centrifuged to collect the sample. The aforementioned dissolved and clarified sample was evaporated at room temperature and then centrifuged to collect the sample. The above sample was placed in a vacuum drying oven (40° C.) and dried overnight, and the crystal form was detected by XRPD, the crystal form of the final product was the crystal form A of the compound of formula (I).

Example 3: Preparation of Crystal Form B of Compound of Formula (I)

The compound of formula (I) (50 mg) was added to a glass bottle, tetrahydrofuran (0.4 mL) was added, and stirred until the solution was clarified. The aforementioned dissolved and clarified sample was evaporated at room temperature, and then centrifuged to collect the sample. The above sample was placed in a vacuum drying oven (40° C.) and dried overnight, and the crystal form was detected by XRPD, the crystal form of the final product was the crystal form B of the compound of formula (I).

Example 4: Solubility Test of Crystal Form A of Compound of Formula (I)

1. Preparation of diluent and mobile phase

Diluent: 300 mL of pure water and 100 mL of pure acetonitrile were accurately measured, and mixed in a 1 L glass bottle, ultrasonically degassed for 10 minutes for use.

Mobile phase A: 0.1% phosphoric acid aqueous solution

For example: 2.0 mL of phosphoric acid was added into 2000 mL of water, and the mixture was ultrasounded for 10 minutes, mixed evenly, and naturally cooled to room temperature, as mobile phase A.

Mobile phase B: acetonitrile.

2. Preparation of the control solution (using crystal form A per se as the control sample)

5 mg of crystal form A was accurately weighed and placed in a sample bottle, and 10 mL of diluent was added, and the mixture was ultrasounded for 5 minutes, naturally cooled to room temperature, mixed evenly, and labeled as working control solution STD-1.

5 mg of crystal form A was accurately weighed and placed in a sample bottle, and 10 mL of diluent was added, and the mixture was ultrasounded for 5 minutes, naturally cooled to room temperature, mixed evenly, and labeled as working control solution STD-2.

3. Preparation of linear solution

The aforementioned working control solution STD-1 was successively diluted by 1 time, 10 times, 100 times, 1000 times and 2000 times, and was labeled as linear solutions L1, L2, L3, L4 and L5.

4. Solubility test 6 mg of crystal form A was accurately weighed respectively and added into 8 mL glass bottle, and then 3 mL of different solvents (0.1N hydrochloric acid solution, 0.01N hydrochloric acid solution, purified water, pH 3.8 buffer solution, pH 4.5 buffer solution, pH 5.5 buffer solution, pH 6.0 buffer solution, pH 7.4 buffer solution, pH 6.8 buffer solution) were accurately added to prepare the suspensions.

A stirrer was added to the above suspensions, and the suspensions were fully stirred at 37° C. in dark. After stirring, the solids in the pH 7.4 buffer solution and the pH 6.8 buffer solution were completely dissolved, 6 mg of crystal form A were accurately weighed respectively, and added to the buffer solutions, and stirred fully again to prepare suspensions. After stirring for 4 hours and 24 hours, samples were taken and centrifuged. The solutions were filtered with a filter membrane and their concentrations were measured by HPLC. The HPLC analysis method was shown in Table 3.

TABLE 3

| HPLC analysis methods | |
|---|---|
| Instrument | Agilent 1200 High Performance Liquid Chromatograph |
| Chromatographic column | Ascentis Express C18 (4.6 mm × 100 mm, 2.7 μm) |
| Mobile phase A | A = 0.1% phosphoric acid aqueous solution |
| Mobile phase B | Acetonitrile |
| Flow rate | 1.5 mL/min |
| Injection volume | 5.0 μL |
| Detection wavelength | 250 nm |
| Column temperature | 40° C. |
| Diluent | 3/1 (V/V) pure water/acetonitrile |
| Run time | 18 min |

| Gradient | Time (min) | A (%) | B (%) |
|---|---|---|---|
| | 0.00 | 95 | 5 |
| | 13.00 | 5 | 95 |
| | 15.00 | 5 | 95 |
| | 15.01 | 95 | 5 |
| | 18.00 | 95 | 5 |

The results are shown in Table 4:

TABLE 4

Solubility test results of crystal form A in 9 vehicles

| | Solubility | |
|---|---|---|
| Vehicle | (4 hrs) (mg/mL) | (24 hrs) (mg/mL) |
| 0.1N HCl | <LOQ | <LOQ |
| 0.01N HCl | <LOQ | <LOQ |
| pH 3.8 buffer solution | <LOQ | <LOQ |
| pH 4.5 buffer solution | 0.001 | 0.001 |
| pH 5.5 buffer solution | 0.066 | 0.066 |
| pH 6.0 buffer solution | 0.214 | 0.204 |
| pH 6.8 buffer solution | 1.961 | 1.840 |
| pH 7.4 buffer solution | 3.820 | 4.049 |
| Purified water | 0.045 | 0.058 |

Note: LOQ means below the detection limit; the above buffer of different pH refers to specific salt solution of each pH.

Conclusion: crystal form A of compound of formula (I) has good solubility in high pH buffer.

Test Example 1: In Vitro Evaluation of Compounds of Formula (I)

1. Preparation of each working solution

1) DMSO was used as the solvent of a 200-fold working solution, the storing solution was diluted to a 200-fold working solution at each administration concentration.

Crystal form A: 0, 0.002, 0.006, 0.02, 0.06, 0.2 and 0.6 mmol/L;

Lesinurad: 0, 0.06, 0.2, 0.6, 2, 6, and 20 mmol/L.

2) Hanks balanced salt solution (without Cl⁻) was used as the solvent for the 2-fold working solution of transport protein URAT1, and then 200-fold working solution in 1) was diluted by 100 times to obtain a 2-fold working solution at each administration concentration.

3) Hanks balanced salt solution (without Cl⁻) was used to prepare a 2-fold working solution of the drug transport protein URAT1 radiolabeled substrate, and then mixed with the same volume of 2-fold working solution of each concentration in 2), and the mixture was mixed evenly for use.

2. Method of Administration 2.1. Uptake Cell Inhibition Experiment

The cell culture medium used in the uptake inhibition experiment was DMEM medium added with 10% FBS (containing penicillin and streptomycin).

After resuscitation and subculture of the human drug transporter-overexpressed cell line (HEK293A-URAT1) and empty vector cells (HEK293A-pcDNA3.1), the adherent cells that grew well were selected, and digested with trypsin to disperse them into single cell suspension. Then the cell density was adjusted to $2.0$-$3.0 \times 10^5$ cells/mL with the culture medium, and then the cell suspension was inoculated into a 24-well cell culture plate at a volume of 1 mL/well. The plate was incubated in an incubator at 37° C., 5% $CO_2$ and saturated air humidity for 2-3 days to make the cells grow throughout each well.

First, the culture medium in the culture plate was removed, and it was washed once with Hanks buffer salt solution (without Cl⁻). After that, Hanks buffer salt solution (without Cl⁻) at 37° C. was added to each well and incubated for 10 min. Then, 500 μL of a solution of probe substrate solution containing radiolabel was used to replace the Hanks buffer salt solution (without Cl⁻) in the 24-well plate and the administration was started. After the administration (2 min), the reaction was terminated with the respective pre-cooled buffer salt solution, and the cells were washed 3 times. Then, 400 μL of 0.1 mmol/L NaOH was added to each well to lyse the cells. The cell lysate was taken into a scintillation vial, and 3 mL of Aquasol-2 scintillation liquid was added, and the radioactive intensity in the sample was measured by using Tri-Carb 2910TR liquid scintillation instrument. In the cell transport test, 3 wells (n=3) were set for each concentration, positive control and mock control.

2.2. Data Processing 2.2.1. Inhibition Calculation

The uptake value of the transporter cells in the administration group only containing the radiolabeled substrate (deducting the uptake value $U_0$ of the background group, i.e., the empty vector cells) was defined as 100% (control, $U_c$), which was used as the standard to calculate the percentage (%) of the uptake value U of each administration group added with the compound to be tested after deducting the background relative to the uptake value $U_c$ of the control group, and calculate the inhibitory rate (IR) for transporter activity at each concentration to express the strength of inhibitory effect of the compound on the transporter. The formula is as follows:

$$IR = 1 - [100 \times (U - U_0)/(U_c - U_0)]\%$$

Three repeats (i.e. n=3) were set for each administration concentration. Mean±standard error (SD) was calculated using statistical formulas in Microsoft® Excel 2010 software.

According to the inhibitory rate (IR) for each transporter at each administration concentration, $IC_{50}$ value, the effect of the compound on the transport activity of the drug transporter was calculated through Prism5.0 in combination with the Forecast function in Microsoft® Excel 2010 software.

2.2.2. Statistical Method

The t-test was used to analyze the difference of the average of each sample (P<0.05 was regarded as significant difference).

3. Experimental Results

The compound of formula (I) and lesinurad had a significant inhibitory effect on the uptake of $^{14}C$-UA mediated by uric acid transporter URAT1 (P<0.001), with $IC_{50}$ of 0.034 μmol/L and 6.01 μmol/L, respectively. The inhibitory effect of the compound of formula (I) on URAT1 was about 177 times that of the reference compound lesinurad, and thus had more significant inhibitory effect.

Test Example 2: Pharmacokinetic Evaluation of the Compound of Formula (I)

Experimental purpose: Plasma pharmacokinetics of male and female SD rats after single intravenous injection and intragastric administration as well as repeated intragastric administration for 8 days for the compound of formula (I).

Experiment Procedure:

1. In this experiment, 12 SD rats, half males and half females, were provided by Beijing Vital River Laboratory Animal Technologies Co., Ltd., and were divided into 2 groups according to the similarity of their body weights, each group had 3 females and 3 males. The details of the administration protocol and blood collection protocol were shown in Table 5 and Table 6, respectively.

TABLE 5

Administration protocol

| Group No. | Number of animals per group Male | Number of animals per group Female | Dosage (mg/kg) | Concentration (mg/mL) | Administration volume (mL/kg) | Solvent | Administration route | Administration frequency |
|---|---|---|---|---|---|---|---|---|
| 1 | 3 | 3 | 2.0 | 1.0 | 2.0 | 5% DMS0 + 95% (10% HP-β-CD) | IV | Single |
| 2 | 3 | 3 | 4.0 | 1.0 | 4.0 | 0.5% (w/v) MC | PO | Single |

All animals fasted every other night before the first day of administration and resumed to be fed 4 hours after the administration.

Note: DMSO means dimethyl sulfoxide; HP-β-CD means hydroxypropyl-β-cyclodextrin; MC means methyl cellulose;

IV means intravenous administration; PO means intragastric administration.

TABLE 6

Blood collection protocol

| Group No. | Animal No. | | Sample time point (hr) |
|---|---|---|---|
| | Male | Female | |
| 1 | R1, R2, R3 | R4, R5, R6 | 0.083, 0.25, 0.5, 0.1, 2, 4, 6, 8, 10, 24 h before and after administration |
| 2 | R7, R8, R9 | R10, R11, R12 | 0.25, 0.5, 1, 2, 4, 6, 8, 10, 24 h before and after administration |

Anticoagulant: $K_2$-EDTA

Sample Collection and Analysis Methods 0.15 mL of blood samples from experimental animals were collected by jugular vein puncture, and immediately transferred to labeled centrifuge tubes containing $K_2$-EDTA (0.5 M), and the plasma was separated by centrifugation within 30 minutes (centrifugation condition: 3000 g, 4° C., 15 minutes). Plasma concentrations were measured using a validated LC/MS/MS analysis method; plasma concentrations were processed using a non-compartment model of WinNonlin™ Version 6.3 (Pharsight, Mountain View, Calif.) pharmacokinetics software, and the pharmacokinetic parameters were calculated using the linear logarithmic trapezoid method.

3. Experimental Results and Conclusions

After intravenous administration of SD rats, the compound of formula (I) was rapidly distributed in the body and slowly cleared. The plasma clearance rate of male rats was 9.76±2.29 mL/min/kg, and the steady state apparent volume of distribution ($Vd_{ss}$) was 1.65±0.440 L/kg, $T_{1/2}$ and $AUC_{0-inf}$ were 2.52±0.671 h and 3530±723 ng·h/mL, respectively; the plasma clearance rate of female rats was 6.41±0.656 mL/min/kg, and the steady state apparent volume of distribution ($V_{dss}$) was 1.55±0.408 L/kg, elimination half-life ($T_{1/2}$) and $AUC_{0-inf}$ were 3.04±1.12 h and 5240±544 ng·h/mL, respectively.

After a single intragastric administration of 4.0 mg/kg of the compound of formula (I) to the SD rats, the peak concentration ($C_{max}$) of male rats was 1130±483 ng/mL, and the $AUC_{0-inf}$ was 2510 ng·h/mL, peak time $T_{max}$ was 0.417±0.144 h, elimination half-life ($T_{1/2}$) was 1.72 h; the peak concentration ($C_{max}$) of female rats was 2110±1350 ng/mL, $AUC_{0-inf}$ was 9010±4670 ng·h/mL, peak time $T_{max}$ was 0.667±0.289 h, and the elimination half-life ($T_{1/2}$) was 3.48±0.835 h. The bioavailability of male rats was 35.6%, and the bioavailability of female rats was 86.0%. (Note: $AUC_{0-inf}$ represents the area under the plasma concentration-time curve from time zero to infinity (extrapolation)).

In conclusion, the compound of formula (I) greatly improves the stability of drug metabolism, and also greatly improves the oral absorption bioavailability of drugs.

What is claimed is:

1. A crystal form A of a compound of formula (I) having characteristic diffraction peaks at 2θ angles of 7.50±0.2°, 13.04±0.2°, and 21.43±0.2° in the X-ray powder diffraction pattern thereof, (I)

2. The crystal form A as defined in claim 1, wherein the crystal form A has characteristic diffraction peaks at 2θ angles of 7.50±0.2°, 9.66±0.2°, 13.04±0.2°, 14.42±0.2°, 17.46±0.2°, 18.57±0.2°, 21.43±0.2°, and 26.18±0.2° in the X-ray powder diffraction pattern thereof.

3. The crystal form A as defined in claim 2, wherein the crystal form A has an XRPD pattern as shown in FIG. 1.

4. The crystal form A as defined in claim 1, wherein the crystal form A has an endothermic peak with an onset point of 169.42±3° C. in the differential scanning calorimetry curve thereof.

5. The crystal form A as defined in claim 4, wherein the crystal form A has a DSC pattern as shown in FIG. 2.

6. The crystal form A as defined in claim 1, wherein the crystal form A has a weight loss of 0.04491% at 100±3° C. in the thermogravimetric analysis curve thereof.

7. The crystal form A as defined in claim 6, wherein the crystal form A has a TGA pattern as shown in FIG. 3.

8. A crystal form B of a compound of formula (I) having characteristic diffraction peaks at 2θ angles of 9.88±0.2°, 10.56±0.2°, and 20.38±0.2° in the X-ray powder diffraction pattern thereof, (I)

9. The crystal form B as defined in claim 8, wherein the crystal form B has characteristic diffraction peaks at 2θ angles of 9.88±0.2°, 10.56±0.2°, 12.23±0.2°, 13.04±0.2°, 14.62±0.2°, 17.57±0.2°, 20.38±0.2°, and 26.89±0.2° in the X-ray powder diffraction pattern thereof.

10. The crystal form B as defined in claim 9, wherein the crystal form B has an XRPD pattern as shown in FIG. 4.

11. The crystal form B as defined in claim 8, wherein the crystal form B has an endothermic peak with an onset point of 163.51±3° C. in the differential scanning calorimetry curve thereof.

12. The crystal form B as defined in claim 11, wherein the crystal form B has a DSC pattern as shown in FIG. 5.

13. The crystal form B as defined in claim 8, wherein the crystal form B has a weight loss of 0.1191% at 120±3° C., and a weight loss of 0.6282% from 120±3° C. to 153.60±3° C. in the thermogravimetric analysis curve thereof.

14. The crystal form B as defined in claim 13, wherein the crystal form B has a TGA pattern as shown in FIG. 6.

* * * * *